(12) United States Patent  (10) Patent No.: US 7,727,739 B2
Whateley  (45) Date of Patent: *Jun. 1, 2010

(54) METHODS FOR MEASURING ENZYME ACTIVITY

(75) Inventor: John G. Whateley, Cardiff (GB)

(73) Assignee: GE Healthcare UK Limited, Amersham (GB)

( * ) Notice: Subject to any disclaimer, the term of this patent is extended or adjusted under 35 U.S.C. 154(b) by 825 days.

This patent is subject to a terminal disclaimer.

(21) Appl. No.: 10/417,543

(22) Filed: Apr. 17, 2003

(65) Prior Publication Data

US 2003/0228609 A1    Dec. 11, 2003

(30) Foreign Application Priority Data

Apr. 19, 2002    (GB) ................................ 0208989.4

(51) Int. Cl.
*C12Q 1/37*    (2006.01)
(52) U.S. Cl. ............................... 435/23; 506/6; 506/11; 506/18
(58) Field of Classification Search ........................ None
See application file for complete search history.

(56) References Cited

U.S. PATENT DOCUMENTS

| 4,598,043 | A |   | 7/1986 | Svendsen |
| 5,108,908 | A | * | 4/1992 | Coves et al. ................ 435/68.1 |
| 5,708,137 | A |   | 1/1998 | Toth et al. |
| 5,807,746 | A |   | 9/1998 | Lin et al. |
| 5,968,479 | A |   | 10/1999 | Ito et al. |
| 6,133,445 | A |   | 10/2000 | Waggoner et al. |
| 6,251,583 | B1 |  | 6/2001 | Zhang et al. |
| 6,323,186 | B1 |  | 11/2001 | Klaubert et al. |
| 6,410,255 | B1 | * | 6/2002 | Pollok et al. ................... 435/23 |
| 6,447,724 | B1 | * | 9/2002 | Jensen et al. ............... 422/68.1 |
| 2001/0004522 | A1 | | 6/2001 | Burke et al. |
| 2001/0005752 | A1 | | 6/2001 | Auer et al. |
| 2005/0176926 | A1 | | 8/2005 | Marme |

FOREIGN PATENT DOCUMENTS

| EP | 0 004 256 | 7/1982 |
| EP | 0 428 000 | 10/1990 |
| EP | 0 231 125 | 8/1992 |
| WO | WO79/00602 | 8/1979 |
| WO | WO 91/16336 | 10/1991 |
| WO | WO 94/28166 | 12/1994 |
| WO | WO 95/25093 | 9/1995 |

(Continued)

OTHER PUBLICATIONS

Karp et al. Time-resloved Europium Fluorescence in Enzyme Activity Measurements: A Sensitive Protease Assay.1983 J. Applied Biochemistry 5:399-403.*

(Continued)

*Primary Examiner*—Christopher Low
*Assistant Examiner*—Christopher M. Gross
(74) *Attorney, Agent, or Firm*—Yonggang Ji

(57) ABSTRACT

The invention relates to fluorescence methods for measuring enzyme activity, in particular enzyme cleaving and joining activities. The invention also relates to fluorogenic substrates which are useful for measuring enzyme activity and as in vitro and in vivo imaging probes.

13 Claims, 9 Drawing Sheets

Digestion of 6-(9-oxo-9H-acridin-10-yl) hexanoyl– AAFFAAF-nitro with Thermolysin

FOREIGN PATENT DOCUMENTS

| WO | WO 98/29562  | 7/1998  |
|----|--------------|---------|
| WO | WO 98/47538  | 10/1998 |
| WO | WO 99/05302  | 2/1999  |
| WO | WO00/73437   | 12/2000 |
| WO | WO 01/41811  | 6/2001  |
| WO | WO 02/056670 | 7/2002  |
| WO | WO 02/081509 | 10/2002 |
| WO | WO 02/099424 | 12/2002 |
| WO | WO 02/099432 | 12/2002 |

OTHER PUBLICATIONS

Fawell et al. Tat-mediated delivery of heterologous proteins into cells. 1994 PNAS 91:664-668.*

Larcchia-Robbio et al. Detection and epitope mapping of immunoreactive human endothelin-1 using ELISA and a surface plasmon resonance-bases biosensor. 1997 Biosensors & Bioelectronics 12:765-778.*

Reymond et al. A general assay for antibody catalysis using acridone as a fluorescent tag. 1996 PNAS 93: 4251-4256.*

Szollosi et al. Application of fluroescence resonance energy transfer in the clinical laboratory: routine and research. 1998 Cytometry 34:159-179.*

Deshayes et al 2005 Cell Mol. Life Sci. 62:1839-1849.*

Faller, T., et al., "A novel acridone derivative for the fluorescence tagging and mass spectrometric sequencing of peptides", *Chem. Commun.*, 1997, p. 1529-1530.

Meldal, M., et al., "Anthranilamide and Nitrotyrosine as a Donor-Acceptor Pair in Internally Quenched Fluorescent Substrates for Endopeptidases: Multicolumn Peptide Synthesis of Enzyme Substrates for Subtilisin Carlsberg and Pepsin", *Analytical Biochemistry*, vol. 195, 1991, p. 141-147.

Bahr, N., et al., "Highly Photoresistant Chemosensors using Acridone as Fluorescent Label", *Tetrahedron Letters*, vol. 38, No. 9, 1997, p. 1489-1492.

Wang, W., et al., "Fluorogenic Peptides Containing Only α-Amino Acids", *Biochemical and Biophysical Research Communications*, vol. 201, No. 2, 1994, p. 835-840.

Hawiger, J., "Noninvasive Intracellular Delivery of Functional Peptides and Proteins", *Current Opinion in Chemical Biology*, vol. 3, 1999, p. 89-94.

Sanders, R., et al., "Quantitative pH Imaging in Cells Using Confocal Fluorescence Lifetime Imaging Microscopy", *Analytical Biochemistry*, vol. 227, Issue 2, Academic Press, Inc., 1995, p. 302-308.

Rojas, M., et al., "Genetic Engineering of Proteins with Cell Membrane Permeability", *Nature Biotechnology*, vol. 16, 1998, p. 370-375.

* cited by examiner

METHODS FOR MEASURING ENZYME ACTIVITY

BACKGROUND OF INVENTION

The present invention relates to fluorescence-based assays for measuring enzyme activity, particularly cleaving and joining reactions.

Assays for measuring enzyme activity, particularly enzyme cleaving activity such as hydrolysis, are widely employed in the biological and pharmaceutical sciences. With the advent of combinatorial chemistry and high throughput screening, there is a growing need for simple, sensitive and cost-effective assays to screen for potential modulators of enzyme activity. Of particular interest to the pharmaceutical industries are methods for detecting proteolytic enzyme cleavage.

Fluorescence-based assays offer significant advantages over radiochemical, ELISA, antibody and more traditional techniques for measuring enzyme cleaving activity in terms of simplicity of handling, sensitivity, cost and ease of automation. Thus, for example, hydrolysable fluorescent substrates are known in the art which, when cleaved, provide fluorescent dyes (EP 0231125) which can be used to measure enzyme activity. Similar substrates are reported in EP 0004256 for use in determining protease activity following proteolytic release of fluorogenic groups. Peptides which are intramolecularly quenched by virtue of synthetic quenching groups (e.g. DABCYL) have been disclosed which have utility as imaging probes (e.g. WO 02/056670). Whilst such fluorogenic labels may provide an effective means of determining enzyme activity they are generally detectable at long wavelengths, typically in the region of 500-600 nm.

More recently there has been considerable interest in the application of fluorescence resonance energy transfer (FRET) assays which involve the use of substrates having donor and quenching acceptors on the same molecule. WO 94/28166 reports the use of such FRET labels attached to a polypeptide substrate which fluoresce more intensely on hydrolysis by a protease. A similar principle is employed in the fluorogenic substrates disclosed in EP 0428000 wherein the peptide substrate has a viral protease enzyme-cleavable site. U.S. Pat. No. 5,708,137 also discloses the use of a fluorogenic substrates to detect viral proteases which comprise internal donor and acceptor/quenching groups.

Methods for fluorescently labelling and quenching peptides have also recently been disclosed. Thus WO 02/081509 describes the use of tryptophan, tyrosine or histidine residues to internally quench fluorescence intensity within fluorescently labelled peptides. The peptides can be used to detect endo- and exo-peptidase activity.

While FRET techniques offer greater sensitivity and reliability for use in screening assays than simple fluorescent intensity techniques, the substrates are considerably more expensive to prepare and purify due to their complex nature. Thus the preparation of FRET labels is demanding in terms of both analytical and/or purification and material costs. Furthermore the only method for distinguishing conventional fluorescent or FRET labels is by their absorption and emission spectra.

Fluorescence lifetime measurements that may be utilised in the present invention offer significant advantages over conventional fluorescence techniques that are based solely on quantifying fluorescence intensity. Fluorescence lifetime is determined from the same spectrally resolved intensity signal, but is additionally resolved in the temporal domain. Fluorescence lifetime techniques provide greater discrimination because the signal is largely unaffected by 'background noise'. A further advantage with this technique is that several different events can be measured simultaneously by selecting labels having distinguishable lifetimes, thus enabling multiplexing. In addition, measurements of fluorescence lifetime are unaffected by concentration effects and photobleaching.

There is therefore a continued need in the biological and pharmaceutical sciences for improved fluorescence-based assays for measuring enzyme cleaving activity. Such assays may have one or more of the following attributes: high sensitivity, good reliability, robustness, simplicity of use, low cost, ease of automation, label specificity and/or more than one form of detection for distinguishing labelled compounds. Preferably the improved assays display more than one of these features and preferably they display all of these features.

It is thus an object of the invention to provide a method of measuring the activity of an enzyme in cleaving a substrate comprising a single fluorescent label and an enzyme cleavable linkage group. It is also an object of the invention to provide a method of screening agents which affect or modulate enzyme cleaving activity. It is a further object of the invention to provide a method of measuring cellular location and distribution of a labelled substrate.

A further object of the present invention is to provide a method for measuring the activity of an enzyme to join a substrate to a reactant.

SUMMARY OF INVENTION

In a first aspect of the present invention, there is provided a method for measuring the activity of an enzyme in cleaving a substrate, the substrate comprising at least one fluorescent label bound to a polymer comprising one or more tyrosine, tryptophan, phenoxy, indolyl or nitro-phenylalanine moieties, the moieties being separated from the at least one fluorescent label by a linkage group cleavable by the enzyme, the method comprising the steps of:

i) measuring the fluorescence lifetime of the at least one label of the substrate in a reaction mixture which facilitates enzyme activity;

ii) adding the enzyme to the reaction mixture, and iii) measuring an increase in fluorescence lifetime of the at least one fluorescent label following step ii);

wherein said increase in fluorescence lifetime indicates substrate cleavage and can be used to determine enzyme activity.

It will be understood by one skilled in the art that the method of the first aspect of the invention involves measuring fluorescence intensity in order to determine fluorescence lifetime.

In a second aspect of the invention, there is provided a method of measuring the activity of an enzyme in cleaving a substrate, the substrate comprising at least one fluorescent label bound to a polymer comprising one or more phenoxy or indolyl moieties, the moieties being separated from the at least one fluorescent label by a linkage group cleavable by the enzyme, the method comprising the steps of:

i) measuring the fluorescence intensity of the at least one label of the substrate in a reaction mixture which facilitates enzyme activity;

ii) adding the enzyme to the reaction mixture, and iii) measuring an increase in fluorescence intensity of the at least one fluorescent label following step ii);

wherein the increase in fluorescence intensity indicates substrate cleavage and can be used to determine enzyme activity.

Suitably, in the method according to the first and/or second aspect, the at least one fluorescent label may be selected from the acridone class of dyes which are described in WO 02/099424.

BRIEF DESCRIPTION OF THE DRAWINGS

The present invention is further illustrated by reference to the following figures and examples in which.

DETAILED DESCRIPTION OF INVENTION

Figure 1:
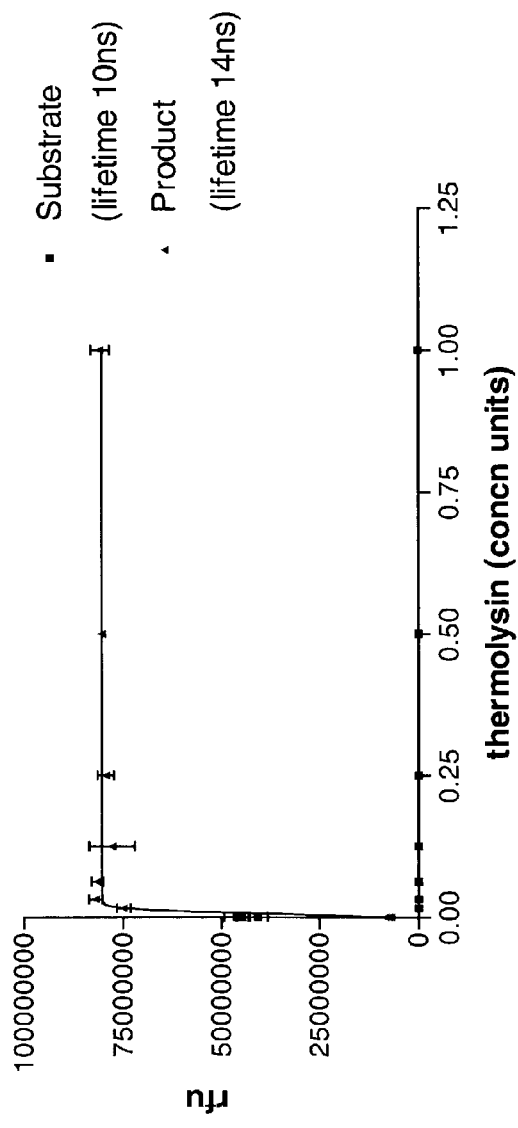
FIG. 1 shows the digestion of 6-(9-oxo-9H-acridin-10-yl) hexanoyl- AAFFAAY (SEQ ID NO:1) with Thermolysin

Acridone dyes suitable for use in the method of the present invention are those having the structure of general formula (I):

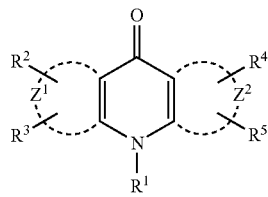

(I)

wherein:

groups $R^2$ and $R^3$ are attached to the $Z^1$ ring structure and groups $R^4$ and $R^5$ are attached to the $Z^2$ ring structure;

$Z^1$ and $Z^2$ independently represent the atoms necessary to complete one or two fused ring aromatic or heteroaromatic systems, each ring having five or six atoms selected from carbon atoms and optionally no more than two atoms selected from oxygen, nitrogen and sulphur;

$R^1$, $R^2$, $R^3$, $R^4$ and $R^5$ are independently selected from hydrogen, halogen, amide, hydroxyl, cyano, amino, mono- or di-$C_1$-$C_4$ alkyl-substituted amino, sulphydryl, carbonyl, $C_1$-$C_6$ alkoxy, aryl, heteroaryl, $C_1$-$C_{20}$ alkyl, aralkyl; the group -E-F where E is a spacer group having a chain from 1-60 atoms selected from the group consisting of carbon, nitrogen, oxygen, sulphur and phosphorus atoms and F is a target bonding group; and the group —$(CH_2—)_n$Y where Y is selected from sulphonate, sulphate, phosphonate, phosphate, quaternary ammonium and carboxyl and n is zero or an integer from 1 to 6.

Suitably, the target bonding group F is a reactive or functional group. A reactive group of the fluorescent dyes according to formula (I) can react under suitable conditions with a functional group of the substrate; a functional group of a compound according to formula (I) can react under suitable conditions with a reactive group of the substrate. By virtue of these reactive and functional groups, the fluorescent dyes according to formula (I) may be reacted with and covalently bond to the substrate, such that the substrate becomes labelled with the fluorescent dye.

Preferably, when F is a reactive group, it is selected from the group consisting of succinimidyl ester, sulpho-succinimidyl ester, isothiocyanate, maleimide, haloacetamide, acid halide, vinylsulphone, dichlorotriazine, carbodiimide, hydrazide and phosphoramidite. Preferably, when F is a functional group, it is selected from hydroxy, amino, sulphydryl, imidazole, carbonyl including aldehyde and ketone, phosphate and thiophosphate.

Suitably, the fluorescent label may be selected from the quinacridone class of dyes which are described in WO 02/099432. Quinacridone dyes suitable for use in the method of the first and/or the second aspect invention are those having the general formula (II):

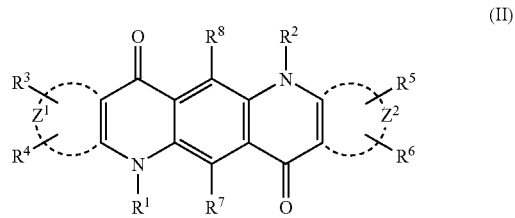

(II)

wherein:

groups $R^3$ and $R^4$ are attached to the $Z^1$ ring structure and groups $R^5$ and $R^6$ are attached to the $Z^2$ ring structure;

$Z^1$ and $Z^2$ independently represent the atoms necessary to complete one or two fused ring aromatic or heteroaromatic systems, each ring having five or six atoms selected from carbon atoms and optionally no more than two atoms selected from oxygen, nitrogen and sulphur;

$R^1$, $R^2$, $R^3$, $R^4$, $R^5$, $R^6$, $R^7$ and $R^8$ are independently selected from hydrogen, halogen, amide, hydroxyl, cyano, amino, mono- or di-$C_1$-$C_4$ alkyl-substituted amino, sulphydryl, carbonyl, carboxyl, $C_1$-$C_6$ alkoxy, aryl, heteroaryl, $C_1$-$C_{20}$ alkyl, aralkyl; the group -E-F where E is a spacer group having a chain from 1-60 atoms selected from the group consisting of carbon, nitrogen, oxygen, sulphur and phosphorus atoms and F is a target bonding group; and the group —$(CH_2—)_n$Y where Y is selected from sulphonate, sulphate, phosphonate, phosphate, quaternary ammonium and carboxyl and n is zero or an integer from 1 to 6.

Suitably, the target bonding group F is a reactive or functional group. A reactive group of the fluorescent dyes according to formula (II) can react under suitable conditions with a functional group of the substrate; a functional group of a compound according to formula (II) can react under suitable conditions with a reactive group of the substrate. By virtue of these reactive and functional groups, the fluorescent dyes according to formula (II) may be reacted with and covalently bond to the substrate, such that the substrate becomes labelled with the fluorescent dye.

Preferably, when F is a reactive group, it is selected from the group consisting of succinimidyl ester, sulpho-succinimidyl ester, isothiocyanate, maleimide, haloacetamide, acid halide, vinylsulphone, dichlorotriazine, carbodiimide, hydrazide and phosphoramidite. Preferably, when F is a functional group, it is selected from hydroxy, amino, sulphydryl, imidazole, carbonyl including aldehyde and ketone, phosphate and thiophosphate.

Preferred examples of acridone and quinacridone dyes (and their corresponding lifetimes (nano seconds)) are shown as compounds (III), (IV), (V), (VI) and (VII) in Table 1 as their NHS (N-hydroxysuccinimidyl) esters:

TABLE 1

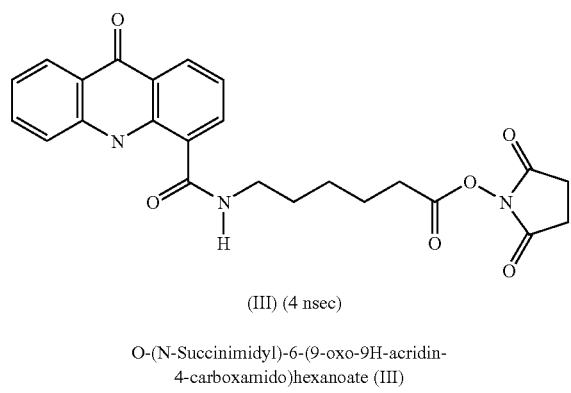

(III) (4 nsec)

O-(N-Succinimidyl)-6-(9-oxo-9H-acridin-4-carboxamido)hexanoate (III)

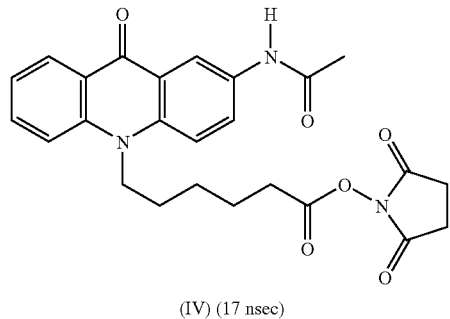

(IV) (17 nsec)

O-(N-Succinimidyl)-6-(2-acetamido-9-oxo-9H-acridin-10-yl)hexanoate (IV)

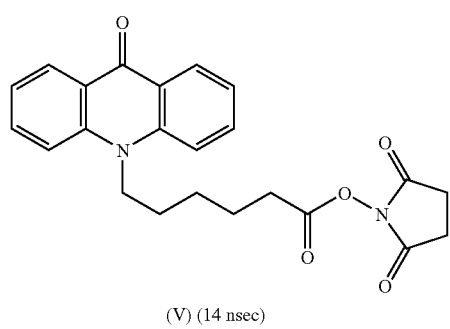

(V) (14 nsec)

O-(N-Succinimidyl)-6-(9-oxo-9H-acridin-10-yl)hexanoate (V)

TABLE 1-continued

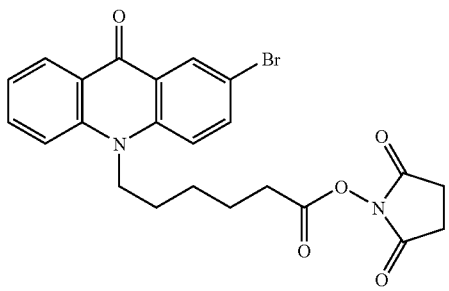

(VI) (8 nsec)

O-(N-Succinimidyl)-6-(2-bromo-9-oxo-9H-acridin-10-yl)hexanoate (VI)

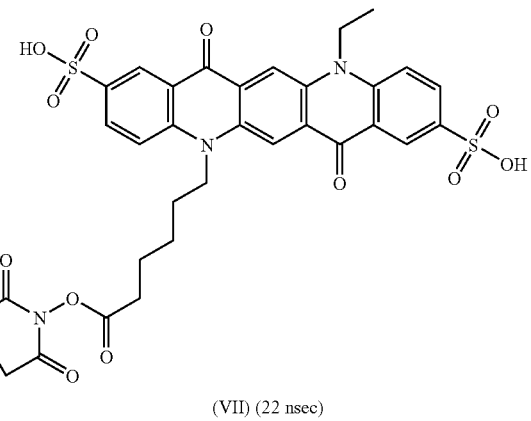

(VII) (22 nsec)

6-(12-Ethyl-7,14-Dioxo-2,9-disulpho-7,14-dihydroquino[2,3-b]acridin-5(12H)-yl) hexanoic acid succinimidyl ester (VII)

A range of fluorescent labels are commercially available which could be bound to the polymer in accordance with the present invention. Examples include, but are not limited to, oxazine (e.g. MR 121, JA 242, JA 243) and rhodamine derivatives (e.g. JA 165, JA 167, JA 169) as described in WO 02/081509. Other examples (as described in WO 02/056670) include, but are not limited to Cy5, Cy5.5 and Cy7 (Amersham); IRD41 and IRD700 (Licor); NIR-1 and IC5-OSu (Dojindo); Alexa fluor 660 & Alexa fluor 680 (Molecular Probes); LaJolla Blue (Diatron); FAR-Blue, FAR-Green One & FAR-Green Two (Innosense); ADS 790-NS and ADS 821-NS (American Dye Source); indocyanine green (ICG) and its analogs (U.S. Pat. No. 5,968,479); indotricarbocyanine (ITC, WO 98/47538); fluorescent quantum dots (zinc sulfide-capped cadimium selenide nanocrystals—QuantumDot Corp.) and chelated lanthanide compounds (fluorescent lanthanide metals include europium and terbium).

The fluorescent label may be attached to the substrate by a variety of methods, such as direct labelling at suitable amino acids. The most important amino acids with regards to labelling are those with ionizable side chains such as aspartic acid, glutamic acid, lysine, arginine, cysteine, histidine and tyrosine. The labelling reagent will have both a group conferring fluorescence and a reactive group involved in conjugation to the target. Some of the most commonly used functional groups are those which react with amines by either acylation or alkylation, such as isothiocyanates, isocyanates, acyl azides and NHS esters. Thio-directed groups such as haloacetates and maleimides, which label primarily at free sulfhydryl group of a cysteine residue, also have utility.

Many protocols have been devised to achieve labelling at a specific site in a synthesised peptide (e.g. Bioconjugate Techniques, G. T. Hermanson, Academic Press (1996)). Reactive dyes are well known and include the NHS esters of the acridone dyes which can be linked to polypeptides in weak carbonate buffers at pH9 or in a nonaqueous environment.

Suitably, the polymer is selected from the group consisting of peptide, polypeptide, protein, nucleic acid, oligonucleic acid, protein nucleic acid, polysaccharide and polyglyceride. Preferably the peptide comprises from 4 to 40 amino acid residues.

In a preferred embodiment of the first or second aspect, the peptide may comprise D-isomers of amino acids which withstand protease digestion, only the cleavage site comprising L-isomers of amino acids which are sensitive to proteolytic activity.

Suitably, the linkage group is cleavable by an enzyme from Enzyme Commission (E.C.) Class 3. A complete listing of enzyme classification can be found on the 'Nomenclature Committee of the International Union of Biochemistry and Molecular Biology's' web page. Preferably the enzyme is a hydrolase enzyme selected from the group consisting of esterase, peptidase, amidase, nuclease and glycosidase.

In a preferred embodiment of the first or second aspect, the enzyme is a peptidase selected from the E.C. Class 3.4. More preferably, the enzyme is selected from the group consisting of angiotensin converting enzyme (ACE), caspase, cathepsin D, chymotrypsin, pepsin, subtilisin, proteinase K, elastase, neprilysin, thermolysin, asp-n, matrix metallo proteinase 1 to 20, papain, plasmin, trypsin, enterokinase and urokinase.

In another embodiment of the first or second aspect, the enzyme is a nuclease preferably selected from the group consisting of EC Class 3.1. More preferably, the nuclease is selected from the group consisting of endonucleases and exonucleases. Typical nucleases include exodeoxyribonuclease III (E.C.3.1.112), exodeoxyribonuclease I (E.C.3.1.11.1), exodeoxyribonuclease V (E.C.3.1.11.5), venom exonuclease (E.C.3.1.15.1), deoxyribonuclease I (E.C.3.1.21.1), deoxyribonuclease II (E.C.3.1.22.1), ribonuclease H (E.C.3.1.26.4), ribonuclease T1 (E.C.3.1.27.3), pancreatic ribonuclease (E.C.3.1.27.5), micrococcal nuclease (E.C.3.1.31.1).

In another embodiment, the enzyme is a glycosidase, preferably selected from the group consisting of E.C. Class 3.2.1. More preferably, the glycosidase is selected from the group consisting of .-amylase (E.C.3.2.1.1), .-amylase (E.C.3.2.1.2), glucan 1,4-.-glucosidase (E.C.3.2.1.3), cellulase (E.C.3.2.1.4), endo-1,3-.-glucanase (E.C.3.2.1.6), oligo-1,6-glucosidase (E.C.3.2.1.10) and lysozyme (E.C.3.2.1.17).

In a third aspect of the present invention, there is provided a method of screening for a test agent whose effect upon the activity of an enzyme in cleaving a substrate is to be determined, the method comprising the steps of:
i) performing the method of the present invention as hereinbefore described in the presence of the agent; and
ii) comparing the activity of the enzyme in the presence of the agent with a known value for the activity of the enzyme in the absence of the agent;

wherein a difference between the activity of the enzyme in the presence of the agent and the known value in the absence of the agent is indicative of the effect of the test agent upon the activity of the enzyme.

Figure 7:
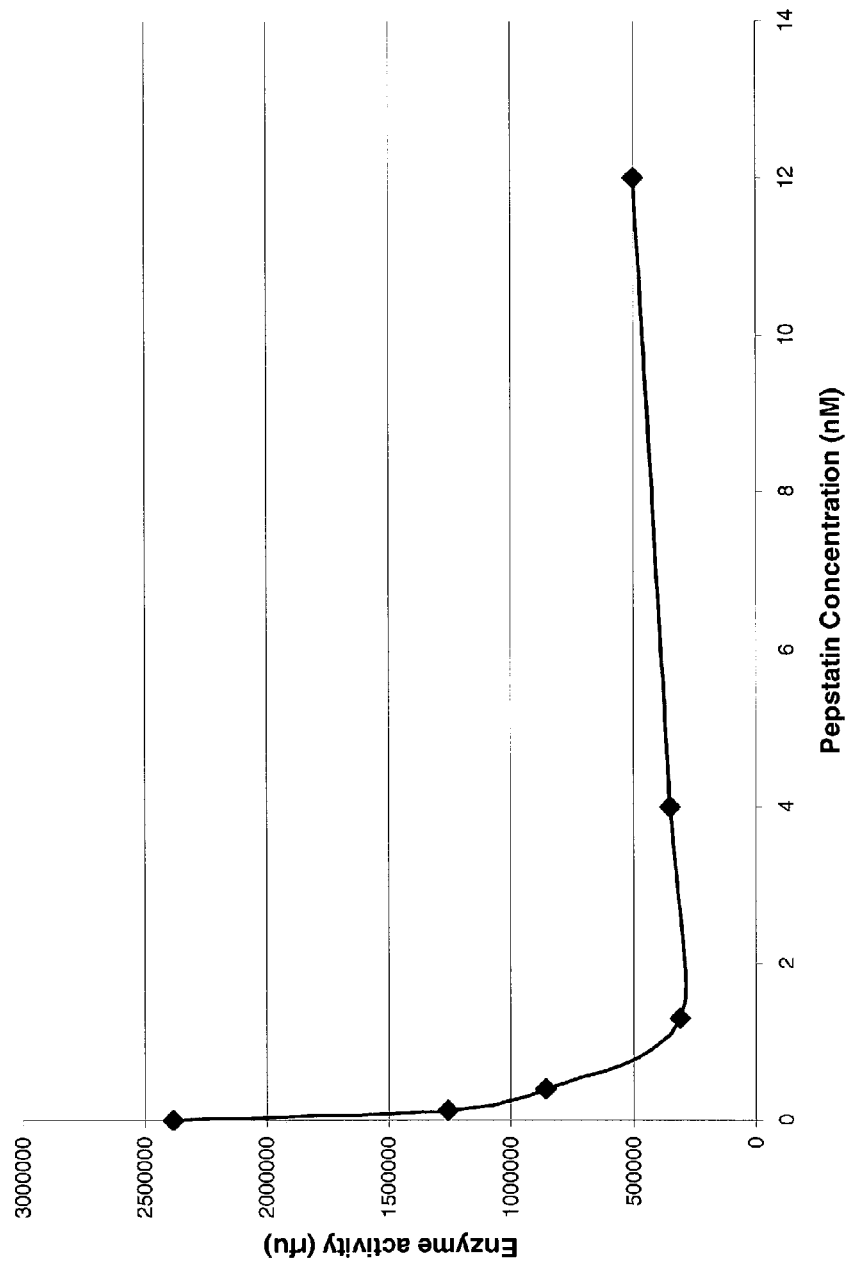
FIG. 7 illustrates the inhibition of the protease enzyme, Cathepsin D, by Pepstatin A

A test agent may be, for example, any organic or inorganic compound such as a synthetic molecule or a natural product (e.g. peptide, oligonucleotide), or a may be an energy form (e.g. light or heat or other forms of electro magnetic radiation). Inhibitors of protease activity can be detected using the method of the third aspect of the invention. For example, the known inhibitor pepstatin A can be readily shown to inhibit cathepsin D enzyme activity using the method of the invention. Thus, in the presence of 12 nM of pepstatin A, cathepsin D activity is some 5 fold less than in the absence of the inhibitor (FIG. 7).

Suitably, the known value is stored upon an electronic database. Optionally, the value may be normalised (for example, to represent 100% activity of the enzyme) and compared to the normalised activity of the enzyme in the presence of the test agent. In this way, only test agents affecting enzyme activity by a certain minimum amount can be selected for further evaluation.

According to a fourth aspect of the present invention, there is provided a method of screening for a test agent whose effect upon the activity of an enzyme in cleaving a substrate is to be determined, the method comprises the steps of:
i) performing the method of the present invention as hereinbefore described in the presence and in the absence of the agent; and
ii) determining the activity of the enzyme in the presence and in the absence of the agent;

wherein a difference between the activity of the enzyme in the presence and in the absence of the agent is indicative of the effect of the test agent upon the activity of the enzyme.

Suitably, the difference in activity between the activity of the enzyme in the absence and in the presence of the agent is normalised, stored electronically and compared with a value of a reference compound. Thus, for example, the difference in activity may be stored as a percentage inhibition (or percentage stimulation) on an electronic database and this value compared to the corresponding value for a standard inhibitor of the enzyme in question. In this way, only test agents meeting a certain pre-determined threshold (e.g. as being as effective or more effective than the reference compound) may be selected as being of interest for further testing.

Suitably the enzyme is a hydrolase enzyme selected from the group consisting of esterase, peptidase, amidase, nuclease and glycosidase.

In a preferred embodiment of the third or fourth aspect, the enzyme is a peptidase selected from the E.C. Class 3.4. More preferably, the enzyme is selected from the group consisting of angiotensin converting enzyme (ACE), caspase, cathepsin D, subtilisin, chymotrypsin, pepsin, proteinase K, elastase, neprilysin, thermolysin, asp-n, matrix metallo proteinase 1 to 20, papain, plasmin, trypsin, enterokinase and urokinase.

In another embodiment of the third or fourth aspect, the enzyme is a nuclease preferably selected from the group consisting of EC Class 3.1. More preferably, the nuclease is selected from the group consisting of endonucleases and exonucleases. Typical nucleases include exodeoxyribonuclease III (E.C.3.1.112), exodeoxyribonuclease I (E.C.3.1.11.1), exodeoxyribonuclease V (E.C.3.1.11.5), venom exonuclease (E.C.3.1.15.1), deoxyribonuclease I (E.C.3.1.21.1), deoxyribonuclease II (E.C.3.1.22.1), ribonuclease H (E.C.3.1.26.4), ribonuclease T1 (E.C.3.1.27.3), pancreatic ribonuclease (E.C.3.1.27.5) and micrococcal nuclease (E.C.3.1.31.1).

In another embodiment of the third or fourth aspect, the enzyme is a glycosidase, preferably selected from the group consisting of E.C. Class 3.2.1. More preferably, the glycosidase is selected from the group consisting of .-amylase (E.C.3.2.1.1), .-amylase (E.C.3.2.1.2), glucan 1,4-.-glucosidase (E.C.3.2.1.3), cellulase (E.C.3.2.1.4), endo-1,3-.-glucanase (E.C.3.2.1.6), oligo-1,6-glucosidase (E.C.3.2.1.10) and lysozyme (E.C.3.2.1.17)

The assay method according to the present invention is preferably performed in the wells of a multiwell plate, e.g. a microtitre plate having 24, 96, 384 or higher densities of wells eg. 864 or 1536 wells. Alternatively, the assay may be conducted in assay tubes or in the microchannels of a multifluidic device. In a typical assay, a sample containing the substance of interest is mixed with the reaction mixture in a well. The reaction is initiated by the addition of enzyme. The reaction is allowed to proceed for a fixed time and stopped with a stop reagent (for example, EDTA).

The reaction mixture can be pre-dispensed into the wells of such a plate.

Typically, enzyme assays are performed under "stopped" conditions. By this it is meant that the reaction is allowed to proceed for a predetermined period and then terminated with a stop reagent. The nature of the stop reagent is typically a strong inhibitor of the enzyme and is often non-specific, for example, EDTA, is used to sequester metal ions that are normally present for enzyme activity. In embodiment of the first and third aspects, assays for enzyme activity either in the presence of or in the absence on a test compound, may be performed under continuous measurement. Because the fluorescence intensity and/or lifetime of the labelled substrate is monitored continuously and can be seen to change continuously, the labelled substrate does not need separation from the product of the enzymatic reaction. A time-course of the reaction may be obtained in this manner, thus allowing kinetic studies to be performed in real time.

In general the assay will consist of several components, typically the enzyme, substrate, metal ions, buffer salts and possibly test or standard inhibitor compounds.

Additionally it may be necessary to run the assays in the presence of low percentages of organic solvents such as DMSO. In this invention it is possible to add any of the reagents to the mix whilst omitting a critical component in any order. This type of reaction can then be monitored for non-specific effects. It is also possible to construct mixture with no enzyme for further controls. Due to the nature of the reactions, it is then possible to add the final component and monitor changes either in real time or by stopping the reaction at some point in the future.

The assay can also be conducted on a variety of body fluids such as blood, mucus, lymphatic fluid, synovial fluid, cerebrospinal fluid, saliva, amniotic fluid, urine, vaginal fluid and semen. Biological samples may, for example, be homogenates, lysates or extracts prepared from whole organisms or parts of an organism. Furthermore, it is possible to assay in media, such as nutrient broth or similar media, where it is possible to grow either eukaryotic or prokaryotic cells.

In a typical example the enzyme will be a matrix metallo proteinase and the substrate will be a specific peptide having a linkage group which is cleavable by this enzyme. The assay will be carried out in a microtitre plate in aqueous conditions in 10 mM $CaCl_2$, 50 mM Tris, 250 nM substrate and 10 μM $ZnCl_2$ at pH 7.2. The substrate will be present at optimal concentration which will be at or below Km which will typically be 0.1-100 μM. Other cofactors may be present at suitable concentration for a given enzyme (e.g. typically at a concentration of 1-10 mM). A typical fluorescent label would be 6-(9-oxo-9H-acridin-10-yl) hexanoic acid (14 ns lifetime), although other examples, such as 6-(9-oxo-9H-acridin-4-carboxamido) hexanoic acid (4 ns lifetime), 6-(2-(acetamido)-9-oxo-9H-acridin-10-yl) hexanoic acid (17 ns lifetime), 6-(2-bromo-9-oxo-9H-acridin-10-yl) hexanoic acid (8 ns lifetime) and/or 6-(12-ethyl-7,14-Dioxo-2,9-disulpho-7,14-dihydroquino[2,3-b]acridin-5(12H)-yl) hexanoic acid, could be used.

The peptide substrate can be easily distinguished from the cleaved products on the basis of differences in the lifetime of the label. Changes in the intensity and the lifetime can be monitored, thus giving a dual parameter fit to this assay. This provides many advantages, for example the biology of the assays can be confirmed by the appearance of the lifetime characteristic for the product and the intensity of the product can be monitored. Another advantage is that the substrate can be monitored by its characteristic lifetime and the substrate intensity can be seen to decrease. Furthermore, it will be possible to determine a quantitative relationship between the intensity of each species, and to directly convert into concentration units for on-line, real time monitoring of the reaction.

Suitably, conventional detection methods can be employed to measure fluorescence intensity and/or the lifetime of the label. These methods include instruments using photo-multiplier tubes as detection devices. Several approaches are possible using these methods; e.g.:

i) methods based upon time correlated single photon counting (cf. Principles of Fluorescence Spectroscopy, (Chapter 4) ed. J R Lakowicz, Second Edition, 1999, Kluwer/Academic Press)

ii) methods based upon frequency domain/phase modulation (cf. Principles of Fluorescence Spectroscopy, (Chapter 5) ed. J R Lakowicz, Second Edition, 1999, Kluwer/Academic Press)

iii) methods based upon time gating (cf. Sanders et al., (1995) Analytical Biochemistry, 227 (2), 302-308).

Measurement of fluorescent intensity may be performed by means of a charge coupled device (CCD) imager, such as a scanning imager or an area imager, to image all of the wells of a multiwell plate. The LEADseeker™ system features a CCD camera allowing imaging of high density microtitre plates in a single pass. Imaging is quantitative and rapid, and instrumentation suitable for imaging applications can now simultaneously image the whole of a multiwell plate.

In a fifth aspect of the present invention there is provided a substrate as hereinbefore described. A typical substrate for thermolysin would be, for example, 6-(9 oxo-9H-acridin-10-yl) hexanoyl -AAFFAAY (SEQ ID NO:1), a typical substrate for Asp-n would be, for example, 6-(9 oxo-9H-acridin-10-yl) hexanoyl -CHLDIIW (SEQ ID NO:2), and a typical substrate for matrix metalloproteinase 3 would be 6-(9-oxo-9H-acridin-10-yl) hexanoyl- RPKPVE(Nva)WRK (SEQ ID NO:3) (all having lifetimes of 10 nano seconds while their products have lifetimes of 14 nano seconds).

In a preferred aspect of the fifth invention, the substrate additionally comprises a cell entry peptide. The cell entry peptide is preferably selected from the group consisting of TAT and Chariot. Other cell entry peptides, or 'carrier' peptides, may be utilised such as those disclosed in WO 01/41811, wherein the carrier peptide comprises from 10 to 15 amino acids and has a core sequence of 3 to 5 hydrophobic amino acids flanked by flanking amino acid sequences, the hydrophobic core comprising proline or leucine residues. Preferably the core sequence is selected from the group consisting of Pro-Leu-Pro-, -Leu-Pro-Leu-, -Leu-Pro-Pro-Leu- (SEQ ID NO:4), -Pro-Pro-Leu-Pro-Pro- (SEQ ID NO:5), -Leu-Leu-Pro-Leu-Leu- (SEQ ID NO:6), -Pro-Leu-Pro-Leu-Pro- (SEQ ID NO:7) and Leu-Pro-Leu-Pro-Leu (SEQ ID NO:8).

Cell entry peptides or signal peptides share a common core motif, which is hydrophobic in nature, and are capable of mediating translocation of peptides and proteins across the cell membrane. The use of such peptides, to facilitate cellular uptake of biological and therapeutic molecules, is well known in the art. Thus, for instance, U.S. Pat. No. 5,807,746 discloses a method for importing biologically active molecules, such as peptides, nucleic acids, carbohydrates, lipids and therapeutic agents, into a cell by administering a complex comprising the molecule to be imported, linked to an importation competent signal peptide. Similarly, Rojas et al. (Nature Biotechnology (1998), 16, 370-375) describes the attachment of a membrane translocating sequence to proteins. The membrane translocating sequence is a specific peptide sequence of twelve amino acids from the hydrophobic region of the signal sequence of Kaposi fibroblast growth factor. Hawiger et al. (Curr. Opinion Chem. Biol. (1999), 89-94) also describes methods for the delivery of functional peptides and proteins into cells, while novel peptide/nucleic acid constructs are disclosed in WO 99/05302 for delivery of intracellular components such as RNA, DNA, enzymes, receptors and regulatory elements.

In a sixth aspect of the present invention there is provided a method of measuring cellular location and distribution of a substrate as hereinbefore described wherein the substrate is capable of being taken up by a living cell, the method comprising the steps of:
i) measuring the fluorescence intensity and/or the fluorescence lifetime of the label of the substrate in a cell free environment;
ii) adding the substrate to one or more cells, and
iii) measuring the fluorescence intensity and/or the lifetime of the fluorescent label following step ii);

wherein an increase in fluorescence intensity and/or fluorescence lifetime indicates substrate cleavage and can be used to determine both enzyme activity and localisation.

The method of the sixth aspect of the present invention is suitable for use in a wide range of cell-based assays. Suitably, the cells may be mammalian, plant, insect, fish, avian, bacterial or fungal in origin. Cell suspensions are particularly suitable for use in the method of the third aspect of the present invention, although other forms of cell culture may be used which are amenable for cell-based assays.

According to a seventh aspect of the present invention, there is provided a method of simultaneously measuring a plurality of different enzyme cleaving activities, the method comprising the use of a plurality of different substrates each bound to a plurality of different fluorescent labels, wherein each label is individually distinguishable from the others by its unique fluorescence emission and/or its fluorescence lifetime. Thus it is possible to distinguish the action of one enzyme on many substrates and/or to identify which of a number of enzymes is present in a sample by measuring cleavage of specific substrates.

The seventh aspect allows multiplex assays to be conducted easily. Thus it is possible to label peptides, for example, with any number of different fluorescent labels, such as the acridone dyes, which can be distinguished on the basis of their fluorescence emission and fluorescence lifetime signal. The labelled peptides are then mixed together with the putative enzymes whose activity it to be measured and changes in fluorescence and lifetime monitored following cleavage of the peptides. Changes in fluorescence emission and lifetime on peptide cleavage will therefore allow identification and quantification of specific enzyme activity, since the fluorescence and/or lifetime signal will be characteristic of particular peptide/dye combinations. In this way, it will be possible to identify which of a number of enzymes are present in a sample and to measure a number of enzyme activities simultaneously.

Preferably the label is selected from the group consisting of 6-(9-oxo-9H-acridin-4-carboxamido) hexanoic acid, 6-(2-(acetamido)-9-oxo-9H-acridin-10-yl) hexanoic acid, 6-(9-oxo-9H-acridin-10-yl) hexanoic acid, 6-(2-bromo-9-oxo-9H-acridin-10-yl) hexanoic acid and 6-(12-ethyl-7,14-Dioxo-2,9-disulpho-7,14-dihydroquino[2,3-b]acridin-5 (12H)-yl) hexanoic acid.

In an eighth aspect of the present invention, there is provided the use of a substrate, as hereinbefore described, for measuring enzyme cleaving activity and/or as an in vitro or in vivo imaging agent. Imaging agents are of use in medical and biological systems for diagnostic purposes and for monitoring therapeutic treatments.

According to a ninth aspect of the present invention, there is provided a kit comprising:
i) a substrate as hereinbefore described; and
ii) an enzyme capable of cleaving the substrate.

According to a tenth aspect of the present invention, there is provided a method of measuring the activity of an enzyme in joining a substrate to a reactant, the substrate comprising at least one fluorescent label and the reactant comprising one or more tyrosine, tryptophan, phenoxy indolyl, or nitro-phenylalanine moieties, the method comprising the steps of:
i) measuring the fluorescence intensity and/or the fluorescence lifetime of the label in a reaction mixture which facilitates enzyme activity;
ii) adding the enzyme to the reaction mixture, and
iii) measuring a decrease in fluorescence intensity and/or lifetime of the fluorescent label following step ii);

wherein the decrease in fluorescent intensity and/or lifetime indicates joining of the substrate to the reactant and can be used to determine enzyme activity.

Thus, for example, covalent attachment of a DNA or RNA molecule to another nucleic acid molecule through the action of a ligase, or the addition of a nucleotide to a DNA or RNA molecule by a polymerase, or the transfer of a chemical moeity (i.e. the reactant) to another molecule (i.e. the substrate) by a transferase such as acetyl transferase, can be detected and measured.

In another example, DNA molecules to be joined are mixed together in aqueous buffer containing ATP in the presence of a DNA ligase. Following incubation, the DNA strands are covalently attached in the correct configuration by formation of phosphodiester linkages in both strands of the duplex. Upon joining, the label moeities are brought into sufficiently close proximity for quenching to occur between the fluorescent dye and the aromatic quenching species which results in a decrease in the fluorescence signal which is proportional to the amount of ligated product formed.

Optionally, the reactant comprises at least one fluorescent label and the substrate comprises one or more tyrosine, tryptophan, phenoxy indolyl or nitro-phenylalanine moieties.

Suitably, the fluorescent label is an acridone dye as hereinbefore described or a quinacridone dye as hereinbefore described.

Preferably, the substrate and/or the reactant is selected from the group consisting of peptide, polypeptide, protein, nucleic acid, oligonucleic acid, protein nucleic acid, polysaccharide and polyglyceride.

In a preferred embodiment of the tenth aspect, the enzyme is a ligase of EC class 6 or a transferase of EC class 2.

According to an eleventh aspect of the present invention, there is provided a method of screening for a test agent whose effect upon the activity of an enzyme in joining a substrate to a reactant is to be determined, the method comprising the steps of:

i) performing the method of the present invention as hereinbefore described in the presence of the agent; and ii) comparing the activity of the enzyme in the presence of the agent with a known value for the activity of the enzyme in the absence of the agent;

wherein a difference between the activity of the enzyme in the presence of the agent and the known value in the absence of the agent is indicative of the effect of the test agent upon the activity of the enzyme. A test agent may be, for example, any organic or inorganic compound such as a synthetic molecule or a natural product (e.g. peptide, oligonucleotide), or a may be an energy form (e.g. light or heat or other forms of electro magnetic radiation).

Suitably, the known value is stored upon an electronic database. Optionally, the value may be normalised (for example, to represent 100% activity of the enzyme) and compared to the normalised activity of the enzyme in the presence of the test agent. In this way, only test agents affecting enzyme activity by a certain minimum amount can be selected for further evaluation.

According to a twelfth aspect of the present invention, there is provided a method of screening for a test agent whose effect upon the activity of an enzyme in joining a substrate to a reactant is to be determined, the method comprising the steps of:

i) performing the method as hereinbefore described in the presence and in the absence of the agent; and ii) determining the activity of the enzyme in the presence and in the absence of the agent;

wherein a difference between the activity of the enzyme in the presence and in the absence of the agent is indicative of the effect of the test agent upon the activity of the enzyme.

Suitably, the difference in activity between the activity of the enzyme in the absence and in the presence of the agent is normalised, stored electronically and compared with a value of a reference compound.

Thus, for example, the difference in activity may be stored as a percentage inhibition (or percentage stimulation) on an electronic database and this value compared to the corresponding value for a standard inhibitor of the enzyme in question. In this way, only test agents meeting a certain predetermined threshold (e.g. as being as effective or more effective than the reference compound) may be selected as being of interest for further testing.

In a thirteenth aspect of the present invention, there is provided a substrate and/or a reactant are as hereinbefore described. In a preferred embodiment, the substrate and/or reactant additionally comprise a cell entry peptide. More preferably, the cell entry peptide is selected from the group consisting of TAT and Chariot. Other cell entry peptides, or 'carrier' peptides, may be utilised such as those disclosed in WO 01/41811, wherein the carrier peptide comprises from 10 to 15 amino acids and has a core sequence of 3 to 5 hydrophobic amino acids flanked by flanking amino acid sequences, the hydrophobic core comprising proline or leucine residues. Preferably the core sequence is selected from the group consisting of Pro-Leu-Pro-, -Leu-Pro-Leu-, -Leu-Pro-Pro-Leu- (SEQ ID NO:4), -Pro-Pro-Leu-Pro-Pro- (SEQ ID NO:5), -Leu-Leu-Pro-Leu-Leu- (SEQ ID NO:6), -Pro-Leu-Pro-Leu-Pro- (SEQ ID NO:7) and Leu-Pro-Leu-Pro-Leu (SEQ ID NO:8).

According to a fourteenth aspect of the present invention, there is provided a method for measuring cellular location and/or distribution of the substrate and/or the reactant as hereinbefore described, wherein the substrate and the reactant are capable of being taken up by a living cell, the method comprising the steps of:

i) measuring the fluorescence intensity and/or the fluorescence lifetime of the label in a cell-free environment;

ii) adding the substrate and the reactant to one or more cells, and iii) measuring the fluorescence intensity and/or the lifetime of the fluorescent label following step ii);

wherein a decrease in fluorescence intensity and/or fluorescence lifetime indicates substrate joining to reactant and can be used to determine both enzyme activity and localisation.

Suitably, the cells are preferably selected from the group consisting of mammalian, plant, insect, fish, avian, bacterial and fungal cells.

In a fifteenth aspect of the present invention, there is provided a method comprising the use of a plurality of different substrates and/or reactants, as hereinbefore described, each bound to a plurality of different labels, wherein each said label is individually distinguishable from the others by its unique fluorescence emission and its fluorescence lifetime thereby enabling simultaneous measurement of a plurality of enzyme joining activities.

Preferably, the label is selected from the group consisting of 6-(9-oxo-9H-acridin-4-carboxamido) hexanoic acid, 6-(2-(acetamido)-9-oxo-9H-acridin-10-yl) hexanoic acid, 6-(9-oxo-9H-acridin-10-yl) hexanoic acid, 6-(2-bromo-9-oxo-9H-acridin-10-yl) hexanoic acid and 6-(12-ethyl-7,14-dioxo-2,9-disulpho-7,14-dihydroquino[2,3-b]acridin-5(12H)-yl) hexanoic acid.

In a sixteenth aspect of the present invention, there is provided the use of a substrate and/or reactant as hereinbefore described for measuring enzyme joining activity or as an in vivo or in vitro imaging agent. Imaging agents, as described for example in WO 02/056670, are of use in medical and biological systems for diagnostic purposes and for monitoring therapeutic treatments.

According to an seventeenth aspect of the present invention, there is provided a composition comprising a substrate and a reactant as hereinbefore described.

According to a eighteenth aspect of the present invention, there is provided a kit comprising:

i) the substrate and reactant as hereinbefore described, and ii) an enzyme capable of joining the substrate to the reactant.

EXAMPLES

It will be readily apparent to those skilled in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

Example 1

Synthesis of 6-(9-oxo-9H-acridin-10-yl) hexanoyl -AAFFAAY-OH (SEQ ID NO:1)

Synthesis was carried out using an ABI 433a synthesiser using solid phase FastMoc chemistry with standard HBTU/DIEA coupling. Secondary protection of the fmoc protected amino acids was used on the following amino acid: Tyr(tBu).

6-(9-oxo-9H-acridin-10-yl) hexanoic acid was coupled to the peptide resin with all protecting groups present using PyAoP, diethylamine and N-methylpyrrolidone. The peptide was cleaved from the resin using 90% trifluoroacetic acid prior to purification.

Purification of 6-(9-oxo-9H-acridin-10-yl) hexanoyl-AAFFAAY-OH (SEQ ID NO:1) was carried out using reverse phase chromatography on a Vydac $C_{18}$ protein and peptide column (250×50 mm) using a water/acetonitrile gradient containing 0.1% trifluoroacetic acid.

The purified peptide was analysed by reverse phase at 400 nm and found to have a C.P of 99.9% and have a monoisotopic $MN^+$ mass of 1051 as expected for this labelled peptide.

Assay for Thermolysin Protease Activity

The protease substrate (6-(9-oxo-9H-acridin-10-yl) hexanoyl-Ala-Ala-Phe-Phe-Ala-Ala-Tyr[AAFFAAY] (SEQ ID NO:1)) was diluted to 100 nM in Tris buffer (100 mM pH 8.0). To the solution (100 µl) of the labelled substrate in a microtitre plate, 10 ng of thermolysin (10 µl volume) was added. The fluorescence baseline prior to protease addition and the subsequent increase in intensity were recorded at appropriate wavelengths. The lifetime of the fluorescent species was also recorded. The results are shown in FIG. 1. Efficient quenching of fluorescence in the intact substrate results in a low signal. Protease-catalysed hydrolysis of the substrate removes this quenching, restoring the fluorescence. The increase in fluorescence intensity can be continuously monitored and is proportional to protease activity. Since the lifetime of the product and substrate are different it is possible to monitor both the appearance of the product and the disappearance of the substrate. The characteristic lifetimes provide a physico-chemical marker of reaction progress.

Assay for Pepsin Protease Activity

Figure 2:
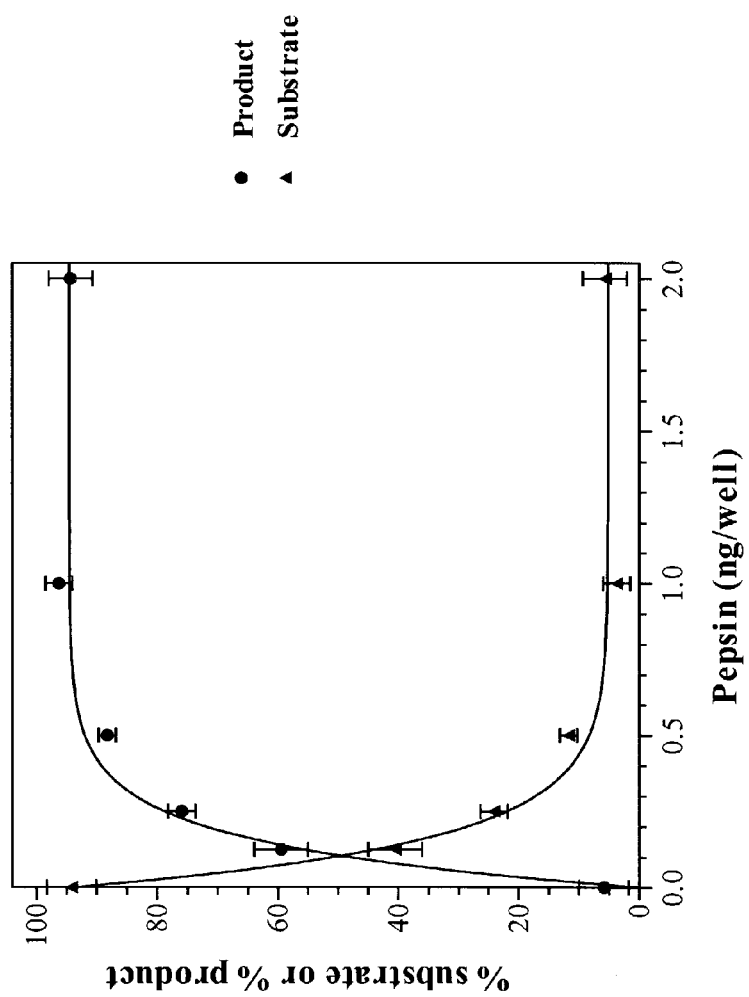
FIG. 2 depicts the digestion of 6-(9-oxo-9H-acridin-10-yl) hexanoyl- AAFFAAY (SEQ ID NO:1) with Pepsin

To 80 µl of the protease substrate, 6-(9-oxo-9H-acridin-10-yl) hexanoic acid-AAFFAAY (SEQ ID NO:1), (125 nM, in 0.1M citrate buffer, pH3.6, 0.005% Tween-20) in triplicate in a microtitre plate, 10 µl of buffer and 10 µl of pepsin (0-2 ng) were added. A no enzyme control (NEC) having 10 µl of buffer in place of enzyme was used. After incubation at ambient temperature, the fluorescence intensity and lifetime were recorded. Deconvolution using a non-linear least-squares analysis algorithm gave the fluorescence lifetimes. Since the lifetimes of substrate (10.3 ns) and product (13.8 ns) are different it was possible to monitor the appearance of product and disappearance of the substrate, the results are shown in FIG. 2.

Assay for Chymotrypsin Protease Activity

Figure 3:
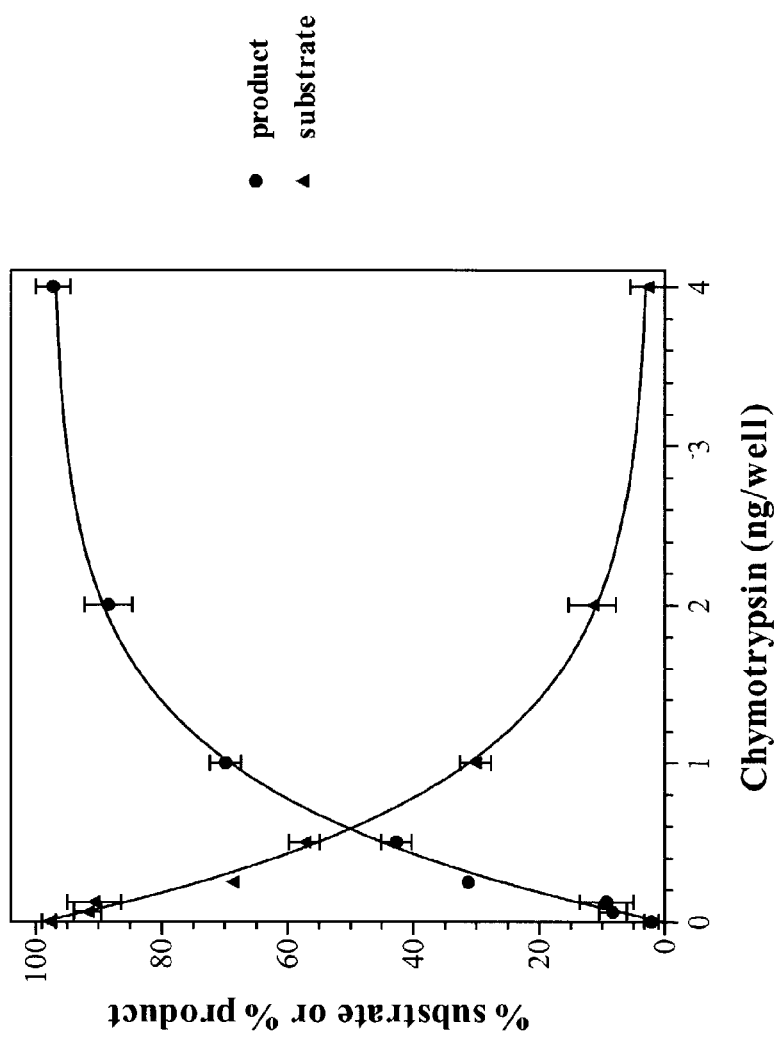
FIG. 3 illustrates the digestion of 6-(9-oxo-9H-acridin-10-yl) hexanoyl-AAFFAAY (SEQ ID NO:1) with Chymotrypsin

To 100 µl of the protease substrate, 6-(9-oxo-9H-acridin-10-yl) hexanoic acid-AAFFAAY (SEQ ID NO:1), (100 nM, in 50 mM Tris buffer, pH7.8; 10 mM $CaCl_2$; 0.005% Tween™ 20) in triplicate in a microtitre plate, 10 µl of chymotrypsin (0-4 ng) was added. A no enzyme control (NEC) having 10 µl of buffer in place of enzyme was used. After incubation at ambient temperature, the fluorescence intensity and lifetime were recorded. Deconvolution using a non-linear least-squares analysis algorithm gave the fluorescence lifetimes. Since the lifetimes of the substrate (11.5 ns) and product (14.5 ns) in Tris buffer are different it was possible to monitor the appearance of product and disappearance of the substrate, the results are shown in FIG. 3.

Example 2

Synthesis of Acridone Labelled Peptide
NH-AAFFAAF (NO2)- NH2 (SEQ ID NO:9)

The peptide was synthesised on an Applied Biosystems model 433A peptide synthesiser using standard Fmoc chemistry. At the end of the synthesis the N-terminal Fmoc group was removed; however the protected peptide was left attached to the solid support, in which form it was reacted with O—(N-succinimidyl)-6-(9-oxo-9H-acridin-10-yl) hexanoate. The labelled peptide was then cleaved from the solid support using standard techniques and then purified by reverse phase HPLC.

50 mg (0.0245 mmol) of the resin bound peptide was weighed into a silanized P87 vial into which was added 500 µl anhydrous DMSO. This was allowed to swell for ½ hour. To this was added 11 mg (1.1 eq) O—(N-succinimidyl)-6-(9-oxo-9H-acridin-10-yl) hexanoate dissolved in 0.5 ml of anhydrous DMSO followed by 1 ml DMSO vial washings and 200 µl (10%) of DIEA. The vial was placed on rollers with light excluded for 16 hrs at ambient temperature (22° C.). The resin was then filtered off using a sintered glass micro funnel (porosity 3), washed with 5 ml dry DMSO, 5 ml methanol and finally 5 ml dichloromethane then dried in vacuo for 2 hrs.

The labelled peptide was then cleaved from the solid support as described below. The resin was placed in a silanized P87 vial into which was added 2 ml of a solution of trifluoroacetic acid (1.90 ml), water (50 µl), and triisopropylsilane (TIS) (50 µl). The mixture was roller stirred for 2 hrs. The solution was then filtered through a sintered glass micro funnel (porosity 3), and the filtrate allowed to collect into 20 ml of ice cold diethyl ether. The pale yellow precipitate was centrifuged down, the supernatant removed, the precipitate redissolved in 1 ml trifluoroacetic acid and reprecipitated in 10 ml ice cold ether. The precipitate was centrifuged down, washed twice with ether then dried in vacuo.

To overcome hydrophobicity problems the dry residue was dissolved in 200 µl DMSO. DMSO was removed by the addition of water to the solution, the vial was then centrifuged, the liquid decanted off, a few more mls. water added and re-centrifuged. This liquid was again decanted off, 1 ml water added and then freeze-dried o/night to yield a dry powder.

Assay for Thermolysin Protease Activity on Nitro-Peptide

Figure 4:
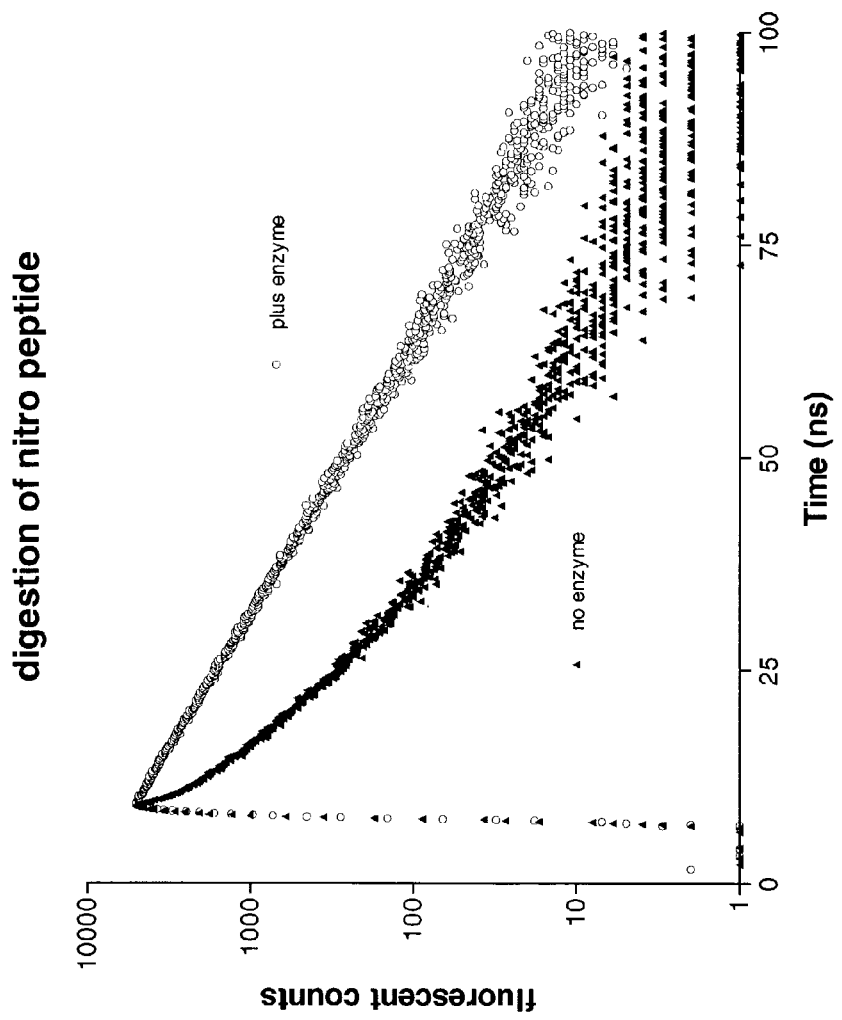
FIG. 4 shows the digestion of 6-(9-oxo-9H-acridin-10-yl) hexanoyl- AAFFAAF-NO2 (SEQ ID NO:9) with Thermolysin

To 2000 µl of the protease substrate, 6-(9-oxo-9H-acridin-10-yl) hexanoic acid- AAFFAAF-nitro (SEQ ID NO:9), (1 µM, in PBS buffer, pH7) in a cuvette, 100 µl of thermolysin (1 Unit/µl) were added. A no enzyme control (NEC) having 100 µl of buffer in place of enzyme was included. After incubation at ambient temperature, the fluorescence intensity and lifetime were recorded. Deconvolution using a stretched exponential non-linear least-squares analysis algorithm gave the fluorescence lifetimes. Since the lifetimes of substrate (2.5 ns) and product (13.7 ns) are significantly different it was possible to monitor the appearance of product and disappearance of the substrate, the results are shown in FIG. 4.

Example 3

Assay for Protease Enzyme

Figure 5:
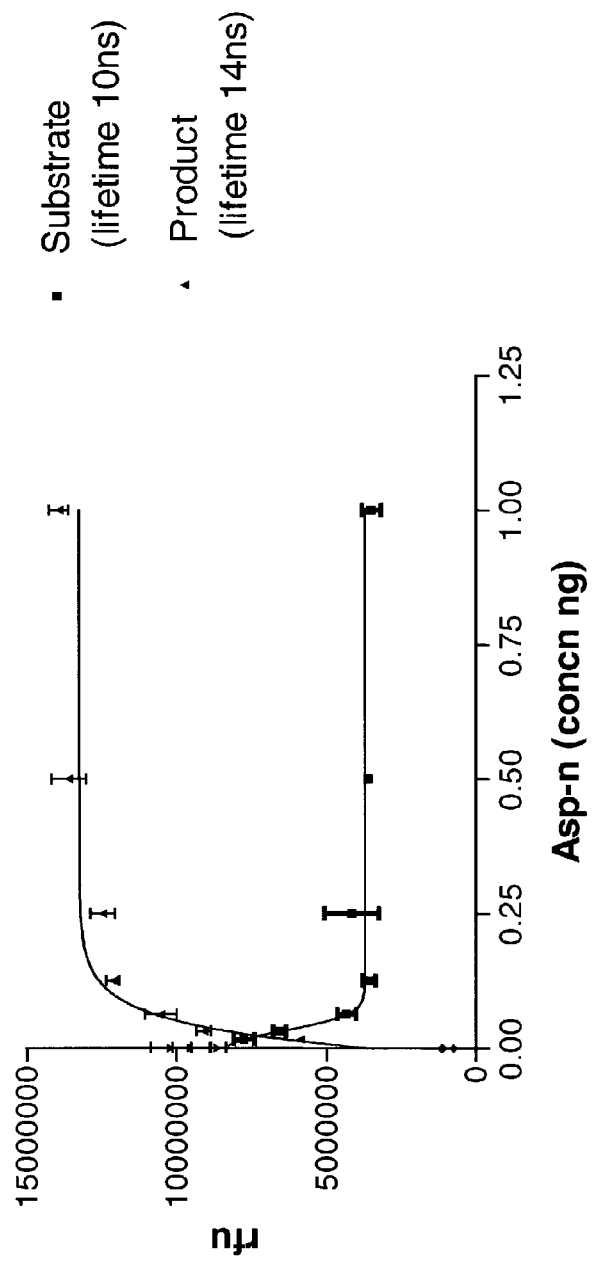
FIG. 5 illustrates the digestion of 6-(9-oxo-9H-acridin-10-yl) hexanoyl -CHLDIIW (SEQ ID NO:2) with Asp-n

The Asp-n protease substrate (6-(9-oxo-9H-acridin-10-yl) hexanoyl- CHLDIIW (SEQ ID NO:2)) was diluted to 100 nM in Tris buffer (100 mM pH 8.0). To the solution (100 µl) of the labelled substrate in a micotitre, 10 ng of enzyme (10 µl volume) was added. The fluorescence baseline prior to protease addition and the subsequent increase in intensity were recorded at appropriate wavelengths. The lifetime of the fluorescent species was also recorded. The results are shown in FIG. 5. Efficient quenching of fluorescence in the intact substrate results in a low signal. Protease-catalysed hydrolysis of the substrate removes this quenching, restoring the fluorescence. The increase in fluorescence intensity can be continuously monitored and is proportional to protease activity. Since the lifetime of the product and substrate are different it is possible to monitor both the appearance of the product and the disappearance of the substrate. The characteristic lifetime provides a physico-chemical marker of reaction progress.

Example 4

Synthesis and Labelling of Acridone-Labelled Peptide RPKPVE (Nva)WRK (SEQ ID NO:3)

The peptide was synthesised on an Applied Biosystems model 431A peptide synthesiser using standard Fmoc chemistry. At the end of the synthesis the N-terminal Fmoc group was removed leaving the protected peptide attached to the solid support, in which form it was reacted with O—(N-succinimidyl)-6-(9-oxo-9H-acridin-10-yl) hexanoate. The labelled peptide was then cleaved from the solid support using standard techniques and further purified by reverse phase HPLC.

100 mg of the resin bound peptide was weighed into a silanized P87 vial to which was added 2 ml anhydrous DMSO and allowed to swell for 2 hours. 17 mg O—(N-succinimidyl)-6-(9-oxo-9H-acridin-10-yl) hexanoate dissolved in 1 ml of anhydrous DMSO followed by 120 µl of diisopropylethylamine was added to the vial. The vial was placed on rollers with light excluded for 20 hrs at ambient temperature (22 C). The resin was then filtered off using a sintered glass micro funnel (porosity 3), washed with 5 ml dry DMSO, 5 ml methanol and finally 5 ml dichloromethane then dried in vacuo for 2 hrs.

Cleavage of the labelled peptide from the solid support was achieved by placing the resin in a silanized P87 vial into which was added 2 ml of an ice cold solution of trifluoroacetic acid (1.90 ml), water (50 l), and triisopropylsilane (TIS) (50 l). The mixture was roller stirred for 90 minutes and allowed to warm to ambient temperature. The mixture was then filtered through a sintered glass micro funnel (porosity 3), and the filtrate allowed to drip into 10 ml of ice cold diethyl ether. The pale yellow precipitate was centrifuged down, the supernatant removed, the precipitate redissolved in 1 ml trifluoroacetic acid and reprecipitated in 10 ml ice cold ether. The precipitate was centrifuged down, washed twice with ether then dried in vacuo.

The crude labelled peptide was purified by HPLC by dissolving in 6 ml water filtered through a 0.45 µm Millipore filter and purifying in 3 increasing volume 'shots' (1 ml, 2 ml and 3 ml) on a 25 cm×1 cm Phenomenex 'Jupiter' C18, 10µ column (code 00G-4055-N0) using a gradient of 0.1% TFA/water to 100% of 0.1% TFA/acetonitrile over 30 minutes and a flow of 4 ml/minute. Detection was at 220 and 400 nm.

The major peak eluted after 17 minutes. This material showed a blue fluorescence under fluorescent room lighting. The material from the eluted peaks was combined and freeze dried in a tared vial to give 35 mg (22 µm) of a pale yellow solid. Mass spectroscopy of this material gave a single peak at 1584 m.u. (calculated molecular wt. of acridone labelled peptide=1584).

Assay for Matrix Metallo Proteinase 3 Enzyme

The MMP-3 substrate (6-(9-oxo-9H-acridin-10-yl) hexanoic acid- Arg-Pro-Lys-Pro-Val-Glu-Nva-Trp-Arg-Lys-NH2 (SEQ ID NO:3) (where Nva=norvaline) (250 nM) was incubated for 2 hours at ambient temperature with MMP-3 enzyme (0±24 nM) in 50 mM Tris buffer pH 7.5 containing 150 mM sodium chloride; 10 mM calcium chloride; 10 µM zinc chloride and 0.05% w/v Brij®-35. The assay was run in black, opaque 96-well plates in final reaction volumes of 100 µl. The fluorescence signals were recorded on a PMT-based lifetime plate reader.

Figure 6:
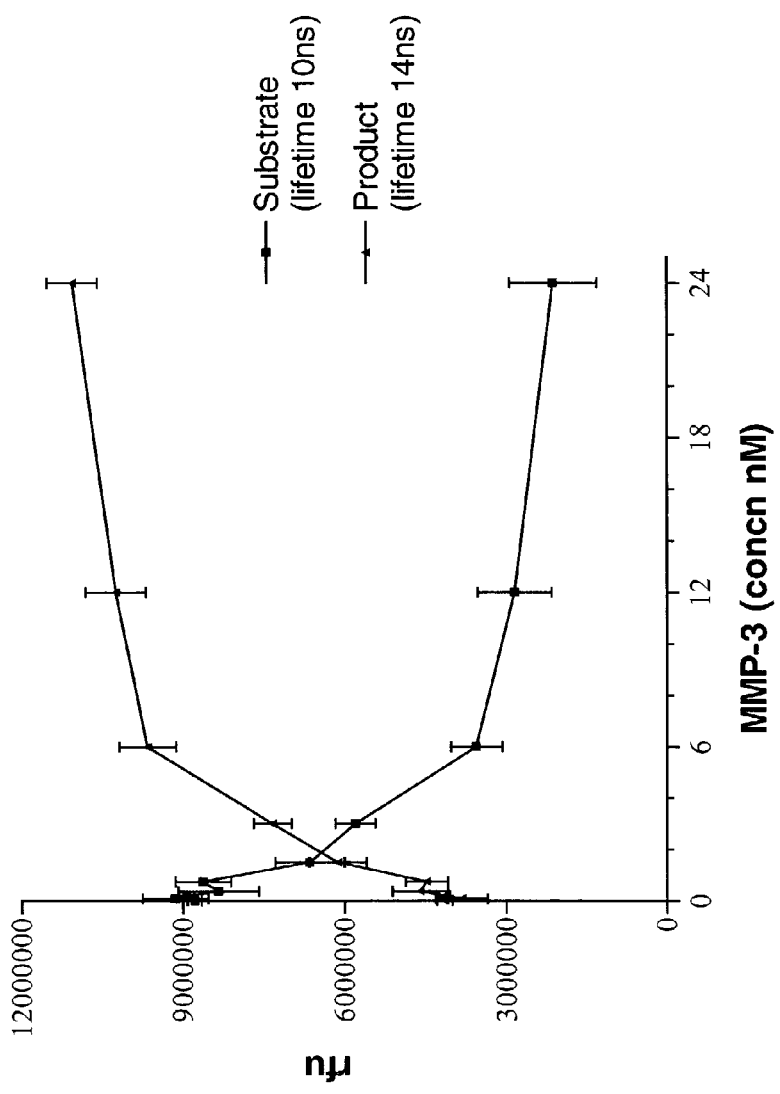
FIG. 6 depicts the digestion of 6-(9-oxo-9H-acridin-10-yl) hexanoyl- RPKPVE(Nva)WRK (SEQ ID NO:3) by Matrix Metalloproteinase 3

The results (FIG. 6) show enzyme-dependant appearance of the product (14 ns lifetime species) and disappearance of the substrate (10 ns lifetime species).

Example 5

Assay for Protease Inhibitor: Inhibition of Cathepsin D Activity

Peptide substrate, 6-(9-oxo-9H-acridin-10-yl) hexanoic acid labelled AAFFAAY (SEQ ID NO:1) (100 nM), was incubated at room temperature with or without bovine kidney cathepsin D enzyme (3 ng/well) in 0.1M sodium citrate buffer containing 0.005% Tween™ 20, pH 3.6. The assay was run in a black, opaque 96-well plates at ambient temperature in final reaction volumes of 100 µl. Fluorescence signals were measured on a PMT-based lifetime plate reader. For inhibition studies, Pepstatin A was used over the range 0-12 nM.

The results are shown in FIG. 7 (each point representing 4 readings) where pepstatin A can be seen to inhibit cathepsin D activity in a dose dependant manner.

Assay for Protease Inhibitor: Inhibition of Pepsin Activity

Figure 8:
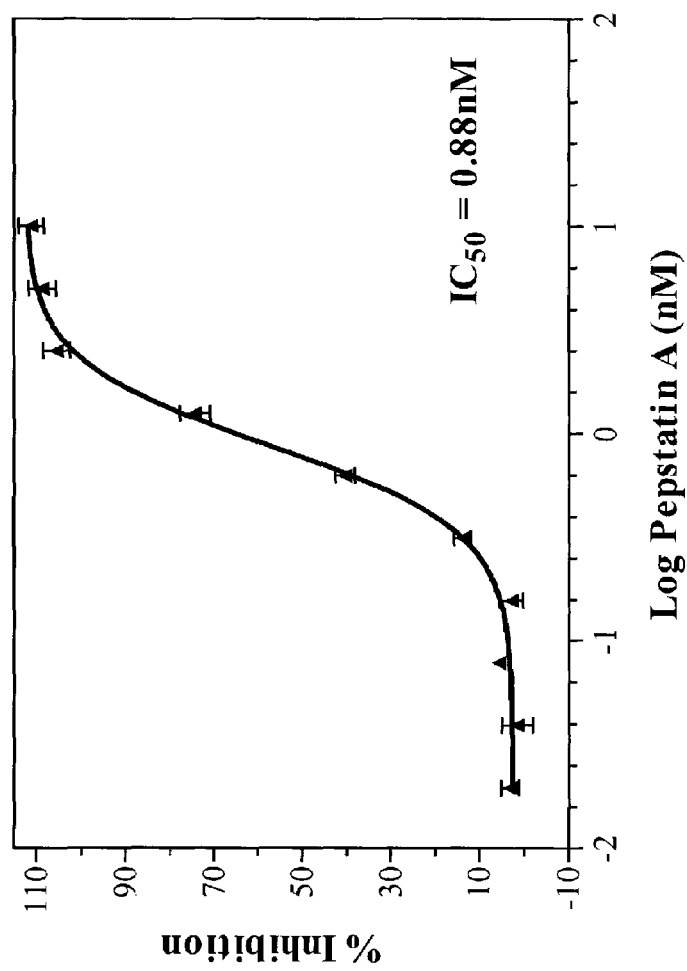
FIG. 8 shows the inhibition of Pepsin by Pepstatin A

To 80 µl of the protease substrate, 6-(9-oxo-9H-acridin-10-yl) hexanoic acid- AAFFAAY (SEQ ID NO:1), (125 nM, in 0.1M citrate buffer, pH3.6, 0.005% Tween-20) in triplicate in a microtitre plate, 10 µl of Pepstatin A and 10 µl of pepsin (0.5 ng) were added. Pepstatin A was used over the range 0-10 nM. After incubation at ambient temperature, the fluorescence intensity and lifetime were recorded. Deconvolution using a non-linear least-squares analysis algorithm gave the fluorescence lifetimes. The results, in FIG. 8, show that Pepstatin A inhibits pepsin digestion of the peptide substrate with an apparent $IC_{50}$ of 0.88 nM.

Assay for Protease Inhibitor: Inhibition of Chymotrypsin Activity

Figure 9:
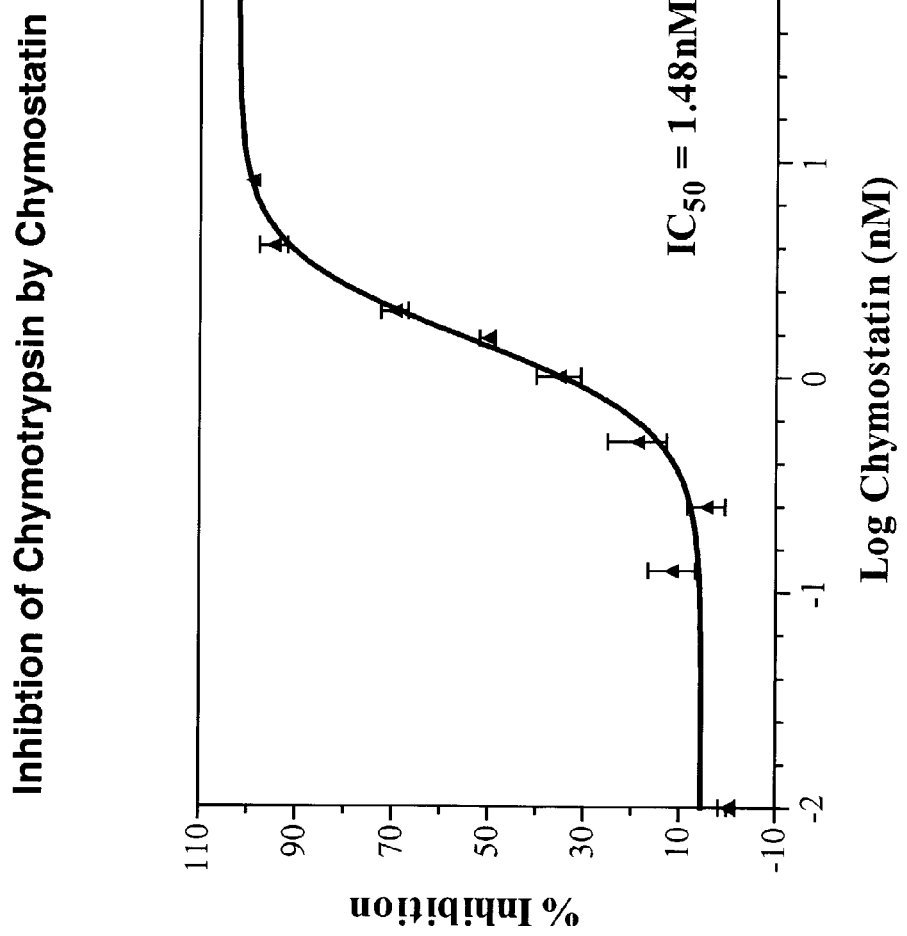
FIG. 9 illustrates the inhibition of Chymotrypsin by Chymostatin

To 80 µl of the protease substrate, 6-(9-oxo-9H-acridin-10-yl) hexanoic acid- AAFFAAY (SEQ ID NO:1), (125 nM, in 50 mM Tris buffer, pH7.8; 10 mM CaCl2; 0.005% Tween™-20) in triplicate in a microtitre plate, 10 µl of chymostatin and 10 µl of chymotrypsin (1 ng) were added. Chymostatin was used over the range 0-100 nM. After incubation at ambient temperature, the fluorescence intensity and lifetime were recorded. Deconvolution using a non-linear least-squares analysis algorithm gave the fluorescence lifetimes. The results, in FIG. 9, show that chymostatin inhibits chymotrypsin digestion of the peptide substrate with an apparent $IC_{50}$ of 1.48 nM

Example 6

Synthesis of 6-(9-oxo-9H-acridin-10-yl) hexanoic acid- RPKPVE (Arg-Pro-Lys-Pro-Val-Glu) (SEQ ID NO:10)

The peptide RPKPVE was synthesised using an ABI 433a synthesiser using solid phase FastMoc chemistry. It was labelled with 6-(9-oxo-9H-acridin-10-yl) hexanoic acid, cleaved from the resin and HPLC-purified in a similar manner to Example 1 above.

The peptide substrate (6-(9-oxo-9H-acridin-10-yl) hexanoic acid- RPKPVE) was diluted to 100 nM in TNC-T buffer (50 mM Tris pH7.5/150 mM NaCl/10 mM CaCl2/0.005% Tween-20).

The lifetime of this solution was determined (2 ml volume in a cuvette) by a time-correlated single photon counting technique (Edinburgh Analytical Instruments FL900CDT spectrometer). Samples were excited at 405 nm using a laser diode, detection being at 450 nm.

Synthesis of 6-(9-oxo-9H-acridin-10-yl) hexanoic acid- RPKPVENvaWRK (Arg-Pro-Lys-Pro-Val-Glu-Nva-Trp-Arg-Lys) (SEQ ID NO:3)

The peptide RPKPVENvaWRK (SEQ ID NO:3) was synthesised in a similar manner to the previous example, labelled with 6-(9-oxo-9H-acridin-10-yl) hexanoic acid and purified.

The labelled peptide (6-(9-oxo-9H-acridin-10-yl) hexanoic acid- RPKPVENvaWRK) (SEQ ID NO:3) was also diluted to 100 nM in TNC-T buffer and the lifetime was similarly recorded.

Comparison of Lifetimes

Deconvolution using a non-linear least squares algorithm gave the lifetimes of each peptide as shown in Table 2:

TABLE 2

Lifetimes of Peptides

| Peptide | Lifetime (ns) |
| --- | --- |
| 6-(9-oxo-9H-acridin-10-yl) hexanoyl-RPKPVE (SEQ ID NO: 10) | 13.9 |
| 6-(9-oxo-9H-acridin-10-yl) hexanoyl-RPKPVENvaWRK (SEQ ID NO: 3) | 12.6 |

Comparison of the lifetimes of the two peptides, one containing a tryptophan residue and one without, showed that the introduction of the tryptophan residue has caused the lifetime to decrease by 1.3 ns. Such a decrease in lifetime would be as expected when two peptides, one of which comprises a fluorescent label, is joined to a second peptide comprising a tryptophan residue which acts to quench the fluorescence lifetime of the label.

It is apparent that many modifications and variations of the invention as hereinabove set forth may be made without departing from the spirit and scope thereof. The specific embodiments described are given by way of example only, and the invention is limited only by the terms of the appended claims.

---

What is claimed is:

1. In a method of measuring the activity of an enzyme in cleaving a substrate, said substrate including at least one fluorescent label bound to a polymer which includes one or more tyrosine, tryptophan, phenoxy, indolyl or nitro-phenylalanine moieties, said moieties being separated from said at least one fluorescent label by a linkage group cleavable by said enzyme, the improvement comprising the steps of:
   i) measuring the fluorescence lifetime of the at least one label of the substrate in a reaction buffer which is suitable for said enzyme to cleave said substrate;
   ii) adding said enzyme to said reaction buffer; and
   iii) measuring any increase in fluorescence lifetime of the at least one fluorescent label following step ii);
wherein said increase in fluorescence lifetime indicates substrate cleavage and is used to determine enzyme activity; further wherein said at least one fluorescent label is an acridone dye of formula:

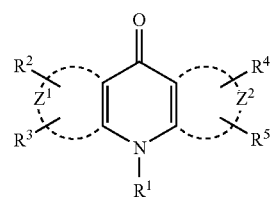

wherein:
  groups $R^2$ and $R^3$ are attached to the $Z^1$ ring structure and groups $R^4$ and $R^5$ are attached to the $Z^2$ ring structure;
  $Z^1$ and $Z^2$ independently represent the atoms necessary to complete one or two fused ring aromatic or heteroaromatic systems, each ring having five or six atoms selected from carbon atoms and optionally no more than two atoms selected from oxygen, nitrogen and sulphur;
  $R^1$, $R^2$, $R^3$, $R^4$ and $R^5$ are independently selected from hydrogen, halogen, amide, hydroxyl, cyano, amino, mono- or di-$C_1$-$C_4$ alkyl-substituted amino, sulphydryl, carbonyl, $C_1$-$C_6$ alkoxy, aryl, heteroaryl, $C_1$-$C_{20}$ alkyl, aralkyl; the group -E-F where E is a spacer group having a chain from 1-60 atoms selected from the group consisting of carbon, nitrogen, oxygen, sulphur and phosphorus atoms and F is a target bonding group; and the group —($CH_2$—)$_n$Y where Y is selected from sulphonate, sulphate, phosphonate, phosphate, quaternary ammonium and carboxyl and n is zero or an integer from 1 to 6 further comprising the use of a plurality of different substrates each bound to a plurality of different labels, wherein each said label is individually distinguishable from the others by its unique fluorescence emission and/or its fluorescence lifetime, thereby enabling simultaneous measurement of a plurality of enzyme cleaving activities.

2. The method of claim 1, wherein said polymer includes one or more phenoxy or indolyl moeities.

3. The method of claim 1, wherein said polymer is selected from the group consisting of peptides, polypeptides, proteins, nucleic acids, oligonucleic acids, protein nucleic acids, polysaccharides and polyglycerides.

4. The method of claim 1, wherein the polymer contains 4 to 40 amino acid residues.

5. The method of claim 1, wherein said linkage group is cleavable by an enzyme of EC Class 3.

6. The method of claim 5, wherein the enzyme is a hydrolase enzyme selected from the group consisting of esterases, peptidases, amidases, nucleases and glycosidases.

7. The method of claim 6, wherein said enzyme is a peptidase selected from the group consisting of angiotensin converting enzyme (ACE), caspase, cathepsin D, chymotrypsin, pepsin, subtilisin, proteinase K, elastase, neprilysin, thermolysin, asp-n, matrix metallo protein 1 to 20, papain, plasmin, trypsin, enterokinase and urokinase.

8. The method of claim 1, wherein said substrate is selected from the group consisting of 6-(9-oxo-9H-acridin-10-yl) hexanoyl -Ala Ala Phe Phe Ala Ala Tyr —OH (SEQ ID No. 1), 6-(9-oxo-9H-acridin-10-yl) hexanoyl-Ala Ala Phe Phe Ala Ala Phe (Nitro) —OH (SEQ ID No. 9), 6-(9-oxo-9H-acridin-10-yl) hexanoyl -Cys His Leu Asp Ile Ile Trp —OH (SEQ ID No. 2) and 6-(9-oxo-9H-acridin-10-yl) hexanoyl-Arg Pro Lys Pro Val Glu (Nva)Trp Arg Lys —OH (SEQ ID No. 3).

9. The method of claim 1, wherein each of said plurality of labels is selected from the group consisting of 6-(9-oxo-9H-acridin-4-carboxamido) hexanoic acid, 6-(2-(acetamido)-9-oxo-9H-acridin-10-yl) hexanoic acid, 6-(9-oxo-9H-acridin-10-yl) hexanoic acid, 6-(2-bromo-9-oxo-9H-acridin-10-yl) hexanoic acid and 6-(12-ethyl-7,14-dioxo-2,9-disulpho-7,14-dihydroquino[2,3-b]acridin-5(12H)-yl) hexanoic acid.

10. In a method of measuring the activity of an enzyme in cleaving a substrate, said substrate including at least one fluorescent label bound to a polymer which includes one or more tyrosine, tryptophan, phenoxy, indolyl or nitro-phenylalanine moieties, said moieties being separated from said at least one fluorescent label by a linkage group cleavable by said enzyme, the improvement comprising the steps of:
  i) measuring the fluorescence lifetime of the at least one label of the substrate in a reaction buffer which is suitable for said enzyme to cleave said substrate;
  ii) adding said enzyme to said reaction buffer; and
  iii) measuring any increase in fluorescence lifetime of the at least one fluorescent label following step ii);

wherein said increase in fluorescence lifetime indicates substrate cleavage and is used to determine enzyme activity;

further wherein said substrate contains a cell entry peptide linked to a labeled polypeptide selected from the group consisting of 6-(9-oxo-9H-acridin-10-yl) hexanoyl -Ala Ala Phe Phe Ala Ala Tyr —OH (SEQ ID No. 1), 6-(9-oxo-9H-acridin-10-yl) hexanoyl -Ala Ala Phe Phe Ala Ala Phe (Nitro) —OH (SEQ ID No. 9), 6-(9-oxo-9H-acridin-10-yl) hexanoyl -Cys His Leu Asp Ile Ile Trp —OH (SEQ ID No. 2) and 6-(9-oxo-9H-acridin-10-yl) hexanoyl-Arg Pro Lys Pro Val Glu (Nva) Trp Arg Lys —OH (SEQ ID No. 3).

11. The method of claim 10, wherein said cell entry peptide is TAT.

12. The method of claim 1, wherein the substrate contains a cell entry peptide linked to a polypeptide selected from the group consisting of 6-(9-oxo-9H-acridin-10-yl) hexanoyl -Ala Ala Phe Phe Ala Ala Tyr —OH (SEQ ID No. 1), 6-(9-oxo-9H-acridin-10-yl) hexanoyl -Ala Ala Phe Phe Ala Ala Phe (Nitro) —OH (SEQ ID No. 9), 6-(9-oxo-9H-acridin-10-yl) hexanoyl -Cys His Leu Asp Ile Ile Trp —OH (SEQ ID No. 2) and 6-(9-oxo-9H-acridin-10-yl) hexanoyl-Arg Pro Lys Pro Val Glu (Nva)Trp Arg Lys —OH (SEQ ID No. 3).

13. The method of claim 12, wherein said cell entry peptide is TAT.

* * * * *

SEQUENCE LISTING

```
<160> NUMBER OF SEQ ID NOS: 10

<210> SEQ ID NO 1
<211> LENGTH: 7
<212> TYPE: PRT
<213> ORGANISM: Artificial Sequence
<220> FEATURE:
<223> OTHER INFORMATION: Substrate for thermolysin
<220> FEATURE:
<221> NAME/KEY: SITE
<222> LOCATION: (1)..(1)
<223> OTHER INFORMATION: Linked to 6-(9 oxo-9H-acridin-10-yl) hexanoyl

<400> SEQUENCE: 1

Ala Ala Phe Phe Ala Ala Tyr
1               5

<210> SEQ ID NO 2
<211> LENGTH: 7
<212> TYPE: PRT
<213> ORGANISM: Artificial Sequence
<220> FEATURE:
<223> OTHER INFORMATION: Substrate for Asp-n
<220> FEATURE:
<221> NAME/KEY: SITE
<222> LOCATION: (1)..(1)
<223> OTHER INFORMATION: Linked to 6-(9 oxo-9H-acridin-10-yl) hexanoyl

<400> SEQUENCE: 2

Cys His Leu Asp Ile Ile Trp
1               5
```

```
<210> SEQ ID NO 3
<211> LENGTH: 10
<212> TYPE: PRT
<213> ORGANISM: Artificial Sequence
<220> FEATURE:
<223> OTHER INFORMATION: Substrate for matrix metalloproteinase
<220> FEATURE:
<221> NAME/KEY: SITE
<222> LOCATION: (1)..(1)
<223> OTHER INFORMATION: Linked to 6-(9 oxo-9H-acridin-10-yl) hexanoyl
<220> FEATURE:
<221> NAME/KEY: MISC_FEATURE
<222> LOCATION: (7)..(7)
<223> OTHER INFORMATION: Xaa refers to Nva which is Norvaline

<400> SEQUENCE: 3

Arg Pro Lys Pro Val Glu Xaa Trp Arg Lys
1               5                   10

<210> SEQ ID NO 4
<211> LENGTH: 4
<212> TYPE: PRT
<213> ORGANISM: Artificial Sequence
<220> FEATURE:
<223> OTHER INFORMATION: Cell entry peptide

<400> SEQUENCE: 4

Leu Pro Pro Leu
1

<210> SEQ ID NO 5
<211> LENGTH: 5
<212> TYPE: PRT
<213> ORGANISM: Artificial Sequence
<220> FEATURE:
<223> OTHER INFORMATION: Cell entry peptide

<400> SEQUENCE: 5

Pro Pro Leu Pro Pro
1               5

<210> SEQ ID NO 6
<211> LENGTH: 5
<212> TYPE: PRT
<213> ORGANISM: Artificial Sequence
<220> FEATURE:
<223> OTHER INFORMATION: Cell entry peptide

<400> SEQUENCE: 6

Leu Leu Pro Leu Leu
1               5

<210> SEQ ID NO 7
<211> LENGTH: 5
<212> TYPE: PRT
<213> ORGANISM: Artificial Sequence
<220> FEATURE:
<223> OTHER INFORMATION: Cell entry peptide

<400> SEQUENCE: 7

Pro Leu Pro Leu Pro
1               5

<210> SEQ ID NO 8
<211> LENGTH: 5
<212> TYPE: PRT
<213> ORGANISM: Artificial Sequence
<220> FEATURE:
```

```
<223> OTHER INFORMATION: Cell entry peptide

<400> SEQUENCE: 8

Leu Pro Leu Pro Leu
1               5

<210> SEQ ID NO 9
<211> LENGTH: 7
<212> TYPE: PRT
<213> ORGANISM: Artificial Sequence
<220> FEATURE:
<223> OTHER INFORMATION: Chemically Synthesized
<220> FEATURE:
<221> NAME/KEY: SITE
<222> LOCATION: (1)..(1)
<223> OTHER INFORMATION: Linked to 6-(9 oxo-9H-acridin-10-yl) hexanoyl
<220> FEATURE:
<221> NAME/KEY: SITE
<222> LOCATION: (7)..(7)
<223> OTHER INFORMATION: Linked to NO2

<400> SEQUENCE: 9

Ala Ala Phe Phe Ala Ala Phe
1               5

<210> SEQ ID NO 10
<211> LENGTH: 6
<212> TYPE: PRT
<213> ORGANISM: Artificial Sequence
<220> FEATURE:
<223> OTHER INFORMATION: Chemically Synthesized
<220> FEATURE:
<221> NAME/KEY: SITE
<222> LOCATION: (1)..(1)
<223> OTHER INFORMATION: Linked to 6-(9 oxo-9H-acridin-10-yl) hexanoic
      acid

<400> SEQUENCE: 10

Arg Pro Lys Pro Val Glu
1               5
```